United States Patent
Luque

(10) Patent No.: US 10,517,716 B2
(45) Date of Patent: Dec. 31, 2019

(54) MULTIFOCAL INTRAOCULAR LENS WITH EXTENDED DEPTH OF FIELD

(71) Applicant: Carl Zeiss Meditec AG, Jena (DE)

(72) Inventor: Sergio Oscar Luque, Berlin (DE)

(73) Assignee: CARL ZEISS MEDITEC AG, Jena (DE)

( * ) Notice: Subject to any disclaimer, the term of this patent is extended or adjusted under 35 U.S.C. 154(b) by 93 days.

(21) Appl. No.: 15/514,069

(22) PCT Filed: Sep. 23, 2015

(86) PCT No.: PCT/ES2015/070688
§ 371 (c)(1),
(2) Date: Mar. 24, 2017

(87) PCT Pub. No.: WO2016/046439
PCT Pub. Date: Mar. 31, 2016

(65) Prior Publication Data
US 2017/0290657 A1 Oct. 12, 2017

(30) Foreign Application Priority Data
Sep. 25, 2014 (ES) .................................. 201431398

(51) Int. Cl.
*A61F 2/16* (2006.01)
*G02C 7/04* (2006.01)
*G02C 7/10* (2006.01)

(52) U.S. Cl.
CPC ............ *A61F 2/1618* (2013.01); *A61F 2/164* (2015.04); *A61F 2/1613* (2013.01);
(Continued)

(58) Field of Classification Search
CPC ...... A62F 2/1618; A62F 2/164; A62F 2/1613; A62F 2/1624; G02C 7/041; G02C 7/102;
(Continued)

(56) References Cited

U.S. PATENT DOCUMENTS

| | | |
|---|---|---|
| 4,636,211 A | 1/1987 | Nielsen et al. |
| 4,955,904 A | 9/1990 | Atebara et al. |

(Continued)

FOREIGN PATENT DOCUMENTS

| | | |
|---|---|---|
| CN | 102448404 A | 5/2012 |
| CN | 102460274 A | 5/2012 |

(Continued)

OTHER PUBLICATIONS

Office Action for Spanish Patent Application No. 201431398 dated Sep. 25, 2014, with English translation, 8 pages.
(Continued)

*Primary Examiner* — David H Willse
*Assistant Examiner* — Tiffany P Shipmon
(74) *Attorney, Agent, or Firm* — Alston & Bird LLP

(57) ABSTRACT

Multifocal intraocular lens with extended depth of field that comprises, in at least one of the surfaces (2), a small zone with a multifocal profile with a defined optical axis (3) and, in the peripheral region and coaxial to the multifocal zone, a ring-shaped opaque mask (1) that partially or totally block light to produce a small aperture effect and, therefore, the multifocal profile has a radius equal or larger than the internal radius of the mask (1), and there is at least one transition between focal zones or one diffractive step inside the internal radius of the mask (1).

16 Claims, 6 Drawing Sheets

(52) U.S. Cl.
CPC .......... *A61F 2/1624* (2013.01); *A61F 2/1659* (2013.01); *G02C 7/041* (2013.01); *A61F 2/1645* (2015.04); *A61F 2/1654* (2013.01); *A61F 2002/1696* (2015.04); *A61F 2250/0053* (2013.01); *G02C 7/102* (2013.01); *G02C 2202/18* (2013.01); *G02C 2202/22* (2013.01)

(58) Field of Classification Search
CPC ............ G02C 2202/22; G02C 2202/18; A61F 2002/1696; A61F 2250/0053; A61F 2/1618; A61F 2/164; A61F 2/1613; A61F 2/1624; A61F 2/1654; A61F 2/1645
See application file for complete search history.

(56) References Cited

U.S. PATENT DOCUMENTS

| | | | |
|---|---|---|---|
| 5,260,727 | A | 11/1993 | Oksman et al. |
| 7,025,455 | B2 | 4/2006 | Roffman |
| 7,287,852 | B2 | 10/2007 | Fiala |
| 7,859,769 | B2 | 12/2010 | Zalevsky |
| 8,696,746 | B2 | 4/2014 | Wanders et al. |
| 2006/0034003 | A1 | 2/2006 | Zalevski |
| 2006/0265058 | A1 | 11/2006 | Silvestrini |
| 2008/0077238 | A1* | 3/2008 | Deacon ................ A61F 2/1613 623/6.16 |
| 2009/0204207 | A1* | 8/2009 | Blum ...................... G02C 7/08 623/4.1 |
| 2009/0234448 | A1 | 9/2009 | Weeber et al. |
| 2010/0312336 | A1 | 12/2010 | Hong et al. |
| 2011/0040376 | A1* | 2/2011 | Christie ................ A61F 2/1613 623/6.17 |
| 2013/0250245 | A1 | 9/2013 | Danta et al. |
| 2013/0268071 | A1* | 10/2013 | Vilupuru ................ A61B 3/102 623/6.17 |

FOREIGN PATENT DOCUMENTS

| | | |
|---|---|---|
| EP | 0246754 | 11/1987 |
| EP | 2113226 | 11/2009 |
| EP | 2168534 | 3/2010 |
| EP | 2219065 | 8/2010 |
| KR | 2002-0033603 | 5/2002 |
| RU | 2436135 C2 | 12/2011 |
| WO | WO 00/52516 | 9/2000 |
| WO | WO 2011/020078 | 2/2011 |
| WO | WO 2013/082545 A1 | 6/2013 |
| WO | WO 2013/123265 | 8/2013 |

OTHER PUBLICATIONS

International Search Report and Written Opinion for corresponding International Application No. PCT/ES2015/070688, dated Feb. 2, 2016.
The State Intellectual Property Office of the P.R.C., First Office Action, including Search Report, for Application No. 20150051820.6, dated Mar. 2, 2018, 10 pages, China.
Korean Intellectual Property Office, Notice of Reasons for Rejection for Korean Patent Application No. 10-2017-7010384, dated Apr. 12, 2019 (5 pages), Korea.

\* cited by examiner

MULTIFOCAL INTRAOCULAR LENS WITH EXTENDED DEPTH OF FIELD

FIELD OF THE TECHNOLOGY

This invention refers to a multifocal intraocular lens with extended depth of field, applied in the ophthalmic field, particularly in the design and development of intraocular lenses. More specifically, this invention makes reference to an intraocular device that presents many benefits to solve presbyopia which is the limitation of focusing at different distances. For that, it is proposed the design of an intraocular lens that comprises a mask to generate a small aperture combined with a multifocal surface whose optical axis can be misaligned up to 1 mm from the geometrical axis.

STATE OF THE ART

Intraocular lenses are devices that are implanted in the eye to solve mainly three problems: refractive error, presbyopia, and in cataract surgery. Presbyopia is the loss of accommodation related with age and it is the impossibility of the human eye to focus objects that are at different distances due to the crystalline lens that does not have the flexibility of the young eye. This lost is gradual and starts to be noticeable after the 45th-48th year of life. At the age of 60, the eye loses practically the whole capacity of accommodation.

In the cataract surgery, the opacified crystalline lens is replaced by another lens to compensate the optical power deficit. The lens that is put to compensate this deficit does not have the dynamic of the natural eye lens (crystalline lens) and so, accommodation cannot be restored.

In any of the previously mentioned conditions, the lens implanted lens can be a simple lens that allows good distance vision although the patient lost the capacity of focusing near objects and patients must wear reading glasses. Another option is to get implanted intraocular lenses that allow patients focusing at different distances and thus avoiding to wear glasses. This is called pseudo-accommodation since the capacity of seeing clear and sharp objects located at different distances is restored by passive ways. The patent U.S. Pat. No. 4,636,211 A, describes the principle of a bifocal refractive lens. The optical power difference between far and near vision is 2.5 diopters and this is what is called addition.

On the other hand, the U.S. Pat. No. 8,696,746 B2 describes a refractive sectorial bifocal lens. This lens has two radii of curvature that vary depending on the angle that a position vector describes, from the center of the lens, but not with the magnitude of this vector. Therefore, this lens does not have a revolutionary profile. Furthermore, it does not present any mask to get a stenopeic effect and it is mentioned that the surfaces have an optical pattern with an axis centered in the lens.

The patent EP2113226B1 makes reference to a diffractive bifocal lens with spherical aberration correction. This aberration is induced by the cornea and has certain impact in the retinal image quality. Then, it is proposed to cancel this aberration by means of the intraocular lens. The aberration values are not personalized for every patient but the lens is manufactured with a value of opposite sign to the mean population value.

The U.S. Pat. No. 7,287,852 B2 claims the invention of an optical zone with a refractive profile configured to have a depth of field of at least 1.1 D and covering an area of approximately 3.14 mm$^2$. Other claims propose a lens that is formed by at least two of the optical zones mentioned in claim 1 with similar features; one of these zones is circular and the other annular. Both zones have a surface of 3.14 mm$^2$ and have the distinctive feature that the optical pathways formed by this lens through adjacent zones from an object to the image have a difference of 1 μm.

The U.S. Pat. No. 7,025,455 B2 claims the design of a refractive multifocal lens that has an annular mask used to block light over the transition zone between the central and peripheral zone. In this invention a pinhole or small aperture is mentioned but it does not have the aim of inducing a stenopeic effect but giving certain binocularity to the lens. This lens is divided into two zones, an internal one entitled pinhole with power for near vision and an external one that form the rest of the lens. The entitled pinhole zone is monofocal and in the transition zone between zones for near and distance vision, it is suggested the use of a mask that has an opacity between 75 and 95% having the objective of avoiding non desired optical effects caused by light that goes through this zone. This mask and the called pinhole do not have as objective the generation of a stenopeic effect or to reduce the numerical aperture.

Every mentioned multifocal lens shows certain collateral effects like the appearance of halos and the reduction of contrast in the image. This cause that many patients are not satisfied after surgery due to these collateral optical effects.

Other principles used in this field to solve presbyopia includes the use of opaque masks in intraocular lenses to totally or partially block light and thus induce phenomenon that benefit vision at different distances.

In this sense, the U.S. Pat. No. 4,955,904A makes reference to the use of an opaque mask in an intraocular lens having as objective to induce a stenopeic effect, and thus, increase the depth of field of the implanted eye. This mentioned opaque mask is part of a monofocal intraocular lens and it does not make any reference to its use in a multifocal system.

On the other hand, the patent WO 201102 0078 A1 claims the design of a monofocal intraocular lens with an aperture that uses an annular mask. This mask induces a stenopeic effect and thus increase the depth of field. The main novelty of this invention is the structure of the body of the lens that permits notably reducing its volume which is very important to allow doctors to implant the lens through a very small corneal incision. This invention does not mention the inclusion of a multifocal surface in the aperture zone.

The patent US 20130238091 A1 describes an intraocular device to be implanted next to an intraocular lens. This device does not have optical power and consist exclusively of an opaque material to block light reducing the effective aperture, and thus, increasing the depth of field. This device has a pattern of micro holes in the surface and a central region free of material that permits light passing through it. The central hole is aligned with the geometrical center of the system.

Another invention described in the patent EP 2168534 A1 uses an opaque mask with different configurations to induce an stenopeic effect. In this invention it is not mentioned the inclusion of a multifocal surface.

In addition to the different reviews with respect to this invention, it has never being proposed the misalignment of the optical axis of the reduced aperture with respect to the geometrical center of the lens for which it is not possible to modify the position of the mentioned aperture in reference to the visual axis of the eye.

Finally, we can also mention the use of variable transmission masks or phase masks.

The U.S. Pat. No. 5,260,727 describes a lens with zones of variable transmittance having a larger transparency in the center and less towards the periphery. According to the claims, this lens permits solving presbyopia by increasing the depth of focus by means of a mask that has variable opacities in radial zones from the center of the lens. This change in the opacity can be continues or discrete (defined zones with different transmittance). The physical principle, described in this patent, is based on that the projected image onto the retina is function of the integral of the light in the focal plane and it is independent of the pupil geometry in monofocal lenses. Then, it is indicated that these changes in the opacity allow the lens to increase the depth of field although it is not mentioned that this is achieved by means of a stenopeic effect.

The U.S. Pat. No. 7,859,769 B2 describes the use of a phase mask. The incorporation of this mask to a possible intraocular lens is intended to increase the depth of focus in up to three diopters for an effective aperture between 1.5 and 5 mm. This aperture, as explained in the patent, is given by the pupil size of the normal population although it is not mentioned to the incorporation of a mask to block light, and thus, reducing and fix the aperture of the lens.

All these lenses offer partial solutions and are susceptible of improvement as it is shown by the lens of this invention, whose advantages are going to be described throughout this document.

BRIEF DESCRIPTION OF THE INVENTION

The invention consists of a multifocal intraocular lens with extended depth of field according to the claims.

In the statement, including claims, it will be named multifocal optical zone to the circular area with diffractive or refractive multifocal profile, whose radius can be up to 1.5 mm. Out of this radius, the lens will not have any multifocality but it will be formed by a spherical, aspherical or flat surface. Furthermore, it will be named useful optical zone to the circular area defined by the internal radius of an opaque mask.

The multifocal intraocular lens with extended depth of field of this invention presents, in at least one of the surfaces, a small zone with a multifocal profile and a defined optical axis and in the peripheral region and coaxial to the multifocal zone a ring-shaped opaque mask that totally or partially blocks light to produce a small aperture effect, and whose multifocal profile has a radius equal or larger than the internal radius of the mask, and has at least one transition between focal zones or one diffractive step inside the internal radius of the mask.

Although the mask blocks visible light that hits it, the circular multifocal area can have a radius equal or larger than the internal radius of the mask to avoid dysphotopsic effects in the border of the useful optical zone and also due to constructive reasons.

The mask could be in the surface of the multifocal profile, inside the body of the lens, in the opposite surface or covering the whole thickness of the optical body. And it is formed by a dye that is printed on the surface of the lens or by an independent component that is attached to the optical body during manufacturing process. A favorite design has an orientation mark in the mask to allow doctors know the position of the optical axis during surgery.

Preferably, the mask will have a transmittance lower than 10% for a wavelength of 550 nm and might be translucent to infrared radiation.

Typical dimensions of the mask will be: between 0.6 and 1.2 mm for the internal radius and 1.5 to 3 mm for the external radius. This implies that the multifocal profile typically has a radius equal or smaller than 1.5 mm.

The lens can have, in addition to the surface with a multifocal profile, an opposite toric surface. The surface with multifocal profile could be described by a diffractive or refractive profile, either bifocal or trifocal.

Two preferable variants, but not limited to them, have been developed. One of them with a multifocal profile has two concentric focal zones; the first zone with a transition radius and the second zone with an external radius larger than the internal radius of the mask. The second variant has a multifocal profile, is formed by two circular sectors with different curvature as described later in this document. Between the two foci of the lens (near-distant vision) there could be a light distribution between 30/70 up to 70/30.

In both cases, the optical axis could be misaligned with respect to the geometrical center of the lens up to 1 mm being 0.2 mm a preferable misalignment.

DESCRIPTION OF THE DRAWINGS

For a better understanding of this invention, the next drawings are included as examples of development.

EMBODIMENTS OF THE INVENTION

Figure 1:
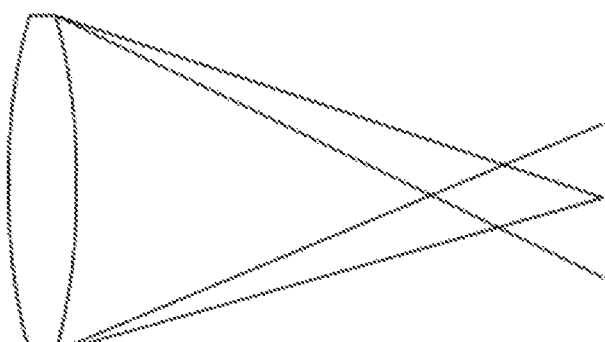
FIG. 1: Schematic drawing showing the image formation of a punctual object by a diffractive lens.

Next, an embodiment of this invention will be described.

This invention comprises the design of an intraocular lens formed by an optical body (5) and having a refractive surface (2) with a multifocal profile whose optical axis (3) is 0.2 mm misaligned from the geometrical center (4) of the lens. The lens comprises a mask (1) which is totally or partially opaque, ring-shaped and coaxial with the multifocal profile axis.

The opaque mask (1) totally or partially blocks light to increase depth of focus by reducing the numerical aperture of the eye. For that, it has an optical transmittance lower than 10% (preferably lower than 3%) for wavelength of 550 nm. Given that to reach an adequate range of focus (between 30 cm and infinity from the observer point of view) is required a too small aperture, we propose to incorporate to this reduced aperture a refractive or diffractive bifocal or trifocal surface (2).

This multifocality permits that the aperture is larger than the one required to generate a stenopeic effect and then, avoiding an extreme reduction of light that reaches the retina. Out of the multifocal zone, the lens does not have any multifocal pattern but it is formed by a spherical or, otherwise, flat surface.

The multifocality does not have the same collateral effect described by patients, who have been implanted with bifocal or trifocal lenses, which cause the perception of halos when light objects are observed in dark backgrounds. For instance, street lights at night. The employed mask in this design has as objective not only to increase the depth of field, but furthermore, reduce the generation of halos.

The lens material must have certain adequate physical and optical properties allowing to be folded, and thus, to be able to be placed in the eye through a small incision, as it is presently done with other intraocular lenses.

In FIG. 1 image formation by a punctual object through a diffractive lens is illustrated as an example, as it is well known in prior art. In the focal point for distant vision both, focus distance image and unfocused near image, converge. The unfocused image on the retina produces contrast reduction of the perceived image and the observation of halos in the already mentioned conditions.

Figure 2:
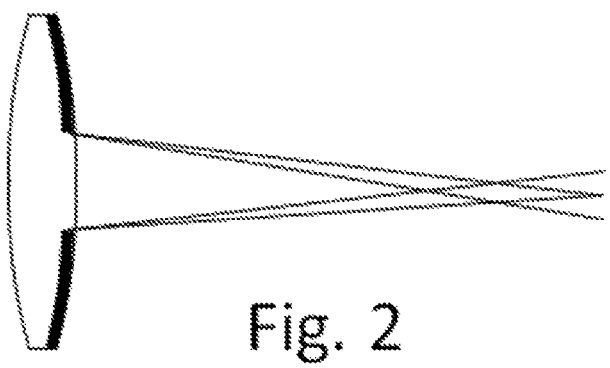
FIG. 2: Same schematic drawing as in FIG. 1 but with a mask.

When a mask (1) is included the cone of transmitted light is reduced and as a result, the effect of the perceived halos is reduced as can be observed in FIG. 2. This is, the impact of the unfocused image on the final resultant image is much smaller. Furthermore, the small aperture cause that the optics has a bigger insensitivity to refractive error post-surgery. As it is well known, refractive errors of around 1 diopter are very common after surgery, mainly in surgeries where the crystalline lens is extracted. The employed mask (1) reduces the impact of defocus on visual quality in comparison with the one observed in patients with conventional intraocular lens either monofocal or multifocal ones.

Even when the amount of light that reaches the retina is also decreased an aperture between 1.2 and 2.4 mm of diameter permits that the transmitted light is enough to do daily tasks.

By means of a simulator of vision through intraocular lenses (disclosed in patent US 20130250245 A 1) we could verify results. This simulator permits to observe object through any intraocular lenses in noninvasive way. This is achieved by means of virtual lens implant. With the use of this device it has been possible to demonstrate that the mask (1) integrated to a bifocal lens increases the depth of focus and reduces halos which are observed in bifocal lenses whose diffractive or refractive profile cover the whole optical area.

Previous inventions do not consider the incorporation of an opaque mask for visible light with a small aperture in combination with a multifocal surface since both were considered incompatible because they can reduce contrast. But studies done with prototypes of this lens comparing commercial available lenses and by means of the mentioned simulator has demonstrated that by combining these two technologies it is possible to achieve a range of pseudo accommodation of 3 diopters with a visual acuity larger than 0.8 (decimal) in the whole mentioned range. The maximum visual acuity was 1.2 for distant vision and 1.0 for near vision.

Figure 3:
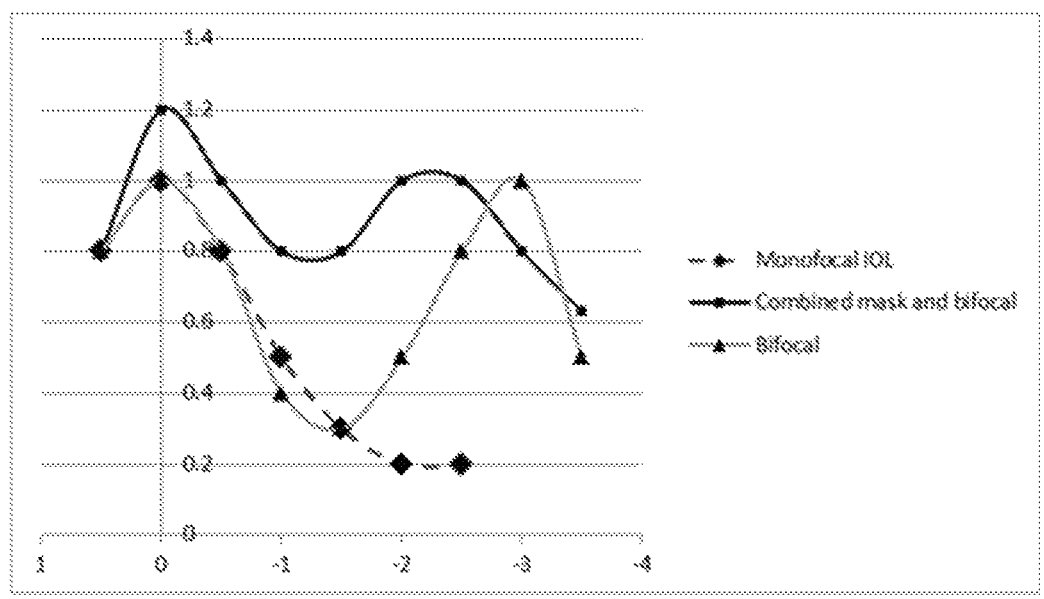
FIG. 3: Accommodation curves obtained with a monofocal lens, a diffractive lens and a diffractive lens with reduced aperture.

FIG. 3 shows visual acuity as a function of the accommodative demand (accommodative curve obtained by negative lenses method) for a monofocal lens, a bifocal lens and a bifocal lens with opaque mask (1) with an internal diameter of 2 mm. In this figure it can be seen the large accommodative range obtained with the bifocal lens with a mask (1). However, the pure bifocal lens shows a big reduction of the visual acuity in the intermediate vision region. In addition, it can be seen the reduced range shown by the monofocal lens. In every case, measurements were performed in the same subject and with a natural pupil of 4 mm in photopic conditions of illumination.

These results show an improvement in the obtained visual acuity but other factors must also be mentioned as halo reduction and higher contrast perceived in photopic conditions. Furthermore, the great improvement in intermediate vision must be emphasized.

Other advantage of this invention is related with the misalignment of the optical axis (3) with respect to the geometrical center (4) of the lens. It is understood by the geometrical center (4) the center of a circle that delimits the body of the lens. In this invention we include the possibility of misaligning the optical axis (3) to permit that the center of the translucent zone coincide or get closer to the achromatic or visual axis of the eye.

This achromatic axis is, in normal condition, very close to the first Purkinje image seen by the surgeon through surgical microscope, used during the implant of intraocular lenses. Generally there is certain difference between the optical axis (3) of an intraocular lens and the first Purkinje image (P1). Therefore, this misalignment would allow surgeons, during surgery, and by rotating the intraocular lens, minimize the distance between the optical axis and P1. Our preferential design includes a misalignment of 0.2 mm between the optical axis (3) of the lens and its geometrical center (4). Therefore, if the first Purkinje reflex is on the geometrical axis (4), the largest difference will be 0.2 mm. On the contrary, if the center of the first Purkinje reflex is away from the geometrical center (4) the lens should be rotated until the difference is minimum.

Only when the first Purkinje reflex (P1) is at 0.2 mm from the geometrical center (4), it will be possible to perfectly align the optical axil (3) with the image P1. Finally, when the image P1 is more than 0.2 mm distant from the geometrical center (4) of the lens, the lens will be rotated to minimize this distance. In case the image P1 is perfectly centered with the geometrical axis, the induced optical misalignment of 0.2 mm is tolerated by the optical system of the eye.

On the contrary, if the image P1 was at, for example, 0.4 mm from the geometrical center (4) of the lens, visual quality would be reduced. But in this case, the optical axis misalignment (3) would allow the distance between the mentioned optical axis and P1 be reduced at 0.2 mm by means of the correct orientation of the lens, and thus, improving the quality of vision.

Figure 4:
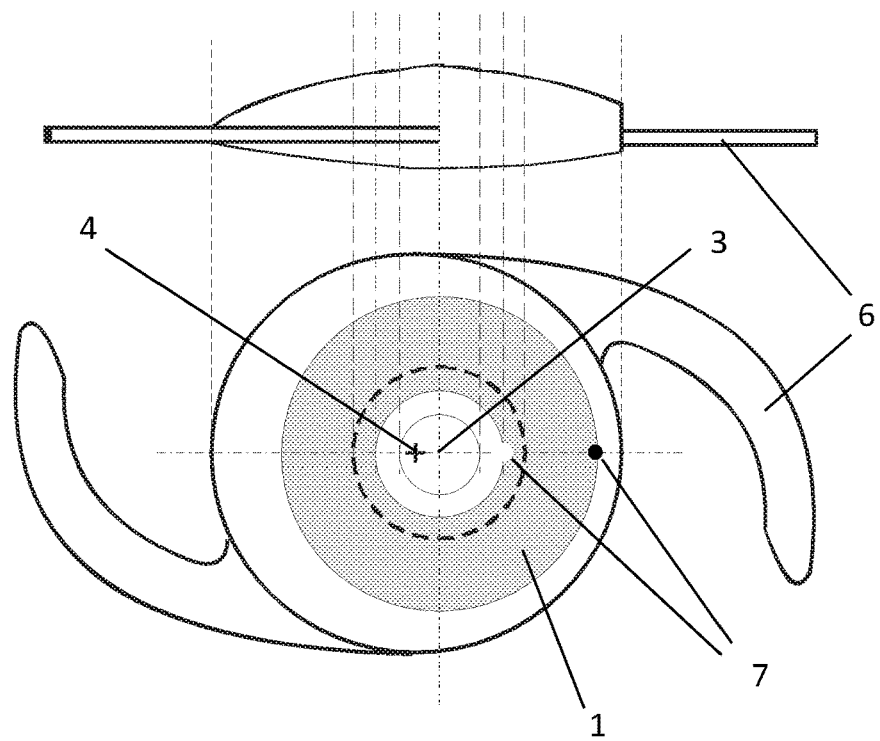
FIGS. 4A and 4B: Two schematic views show two preferential designs where the optical axis is misaligned with respect to the geometrical center indicated with a small cross.
Figure 4:
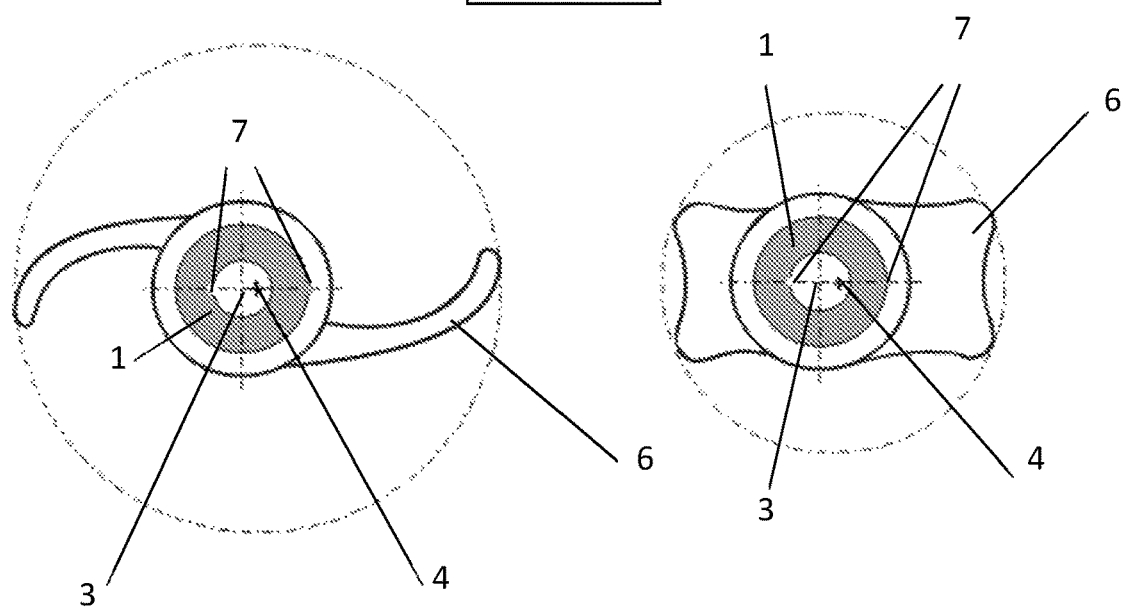

In FIGS. 4A and 4B two preferential design, but not limited to them, are shown where the optical axis is misaligned with respect to the geometrical center indicated with a small cross. This cross is not part of the design and during surgery its exact position is unknown, but it is irrelevant for practical purposes.

In the example shown in FIG. 4A the misalignment of the optical axis is achieved by decentering the optical axis from the body of the lens. In FIG. 4B, it can be seen an example of misalignment produced by an asymmetry of the haptics, which is obtained by means of designing one of them larger than the other as much for haptics C-shaped, plate, or any other model. In C-shaped models, it will be more difficult to specify the displacement of the optical axis since other tensions intervene which could modify the position.

Figure 5:
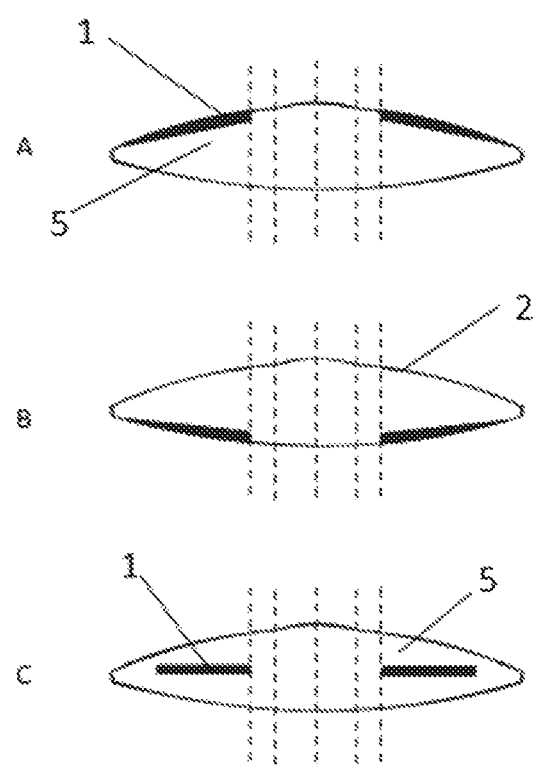
FIG. 5: Possible locations of the mask: A) in the surface with multifocal profile, B) in the surface with monofocal profile and C) in the optical body.

The opaque mask (1) used in this lens can be located at the surface, in the optical body (5) of the lens or can be formed by a component that is separately manufactured to the lens and it is joined to the optical body for some chemical or physical method. FIG. 5 shows possible different options to join together the mask (1) to the optical body (5) of the lens. The shown examples in this figure correspond with a lens whose optical axis (3) coincide with the geometrical axis (4) only for practical purposes although same considerations for misalignment before explained also apply. It is also possible to have a mask that has the thickness of the optical body (5).

The preferential design corresponds with the one that has the mask (1) in the surface with multifocal profile which can be the anterior or posterior surface of the implanted lens.

Figure 6:
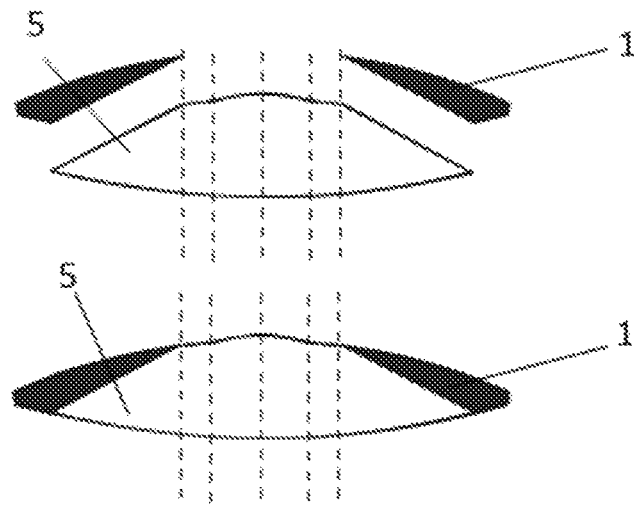
FIG. 6: Optical bodies and mask: A) separated; B) joined

Another proposal of this invention, but not limited to it, is to manufacture the lens using two bodies with different optical features and join them together by a physical, chemical or mechanical way. This manufacturing procedure would allow separately machining or molding of these two components. FIG. 6 shows an example of this design.

In a preferential design, but not limited to it, the opaque body that forms the mask (1) would be formed by an infrared translucent material to permit to capture OCT (Optical Coherent Tomography) images, a very important imaging technique to diagnose the retina. Furthermore, it would allow doctors to perform capsulotomies that require the use of Nd:YAG laser.

With respect to the optical body (5), even when both diffractive and refractive surfaces would improve the depth of focus, our preferential design, but not limited to it, make use of a refractive surface. The main reason is that high diffractive orders have two main collateral unwanted effects. On one hand, they reduce useful light between 10 to 20% decreasing, by this way, the contrast of the image. On the other hand, this useless light is produced by high diffractive orders that focus the image at unwanted distances causing, sometimes, a major perception of halos.

Furthermore, it should be pointed out that diffractive optic has as principal advantage, regarding refractive surfaces, its light distribution independency with respect to pupil size. But in this invention, the small aperture will be, under normal conditions, smaller that the natural pupil of the patient, and therefore, light changes due to pupil size changes are not expected.

Another advantage given by a refractive surface is the possibility of applying polish treatments to the surface which cannot be applied in most of diffractive lenses. We could observe by means of the implant IOL simulator a big difference between polished and unpolished lenses. Unpolished intraocular lenses showed a larger amount of light scattering due to the roughness of the surface. Even when this might have a small impact in lenses with conventional sizes, in this case with a small aperture it is essential to limit all the potential loss of energy sources that, furthermore, cause contrast reduction.

Our preferential design, but not limited to it, comprise a refractive bifocal surface with light distribution of 50/50. This combination of small aperture and bifocal optic is sufficient to give to patients an adequate image contrast, allowing sharp vision, even in low illumination condition. Curvatures could give an addition between 1 to 4 D. This addition is the power difference between the zones of the multifocal surface.

The multifocal zone is surrounded by a circle of radius RM equal or larger than the internal radius of the mask. In a preferential design, RM is equal to the internal radius of the mask with a diameter of 2 mm.

If we call RI the internal radius of the mask (1), RT the transition radius where a change in the curvature is produced (RI>RT), two defined optical regions are determined by the radiuses RT and RI. The ratio between the areas determines light distribution between focal points for near and distant vision. To have light distribution of approximately 50/50, radius RT must be 0.707 times RI.

Figure 7:
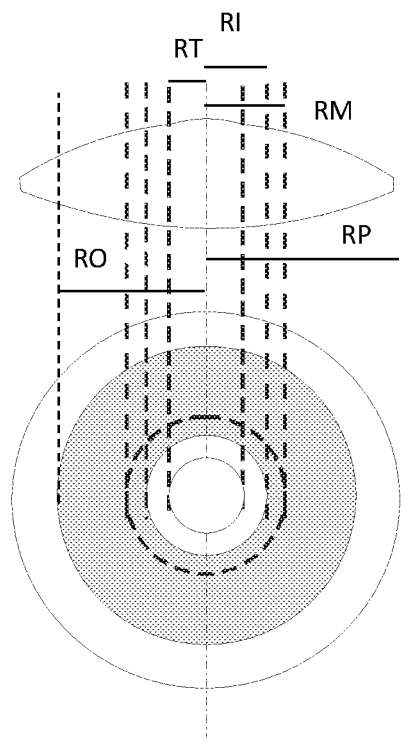
FIG. 7: Examples of a lens with concentric focal zones.

In the top view of FIG. 7 it can be seen the opaque mask to visible light and the two optical regions. The distribution of light can be compressed in a range between 30/70 and 70/30 between far and near vision respectively, where the internal region could be for near or distance vision as it will be explained.

Generally, the internal radius of the mask (1) RI will be in a range between 0.6 to 1.2 mm. The external radius RO can be between 1.5 and 3 mm. As preferential values, an internal radius of 0.9 mm and an external radius of 2.4 mm are suggested. The body of the lens could be formed by an optical radius RP ranging between 2.5 and 3.5 mm, preferably 3 mm.

This intraocular lens is defined by means of two surfaces:

The inferior surface could be spherical or aspherical and have certain toricity to correct astigmatism, although for practical purposes and due to the small aperture, the use of aspherical surfaces does not introduce a big benefit. This surface will have a curvature radius that, in addition to the superior surface will determine the power of the lens.

Figure 8:
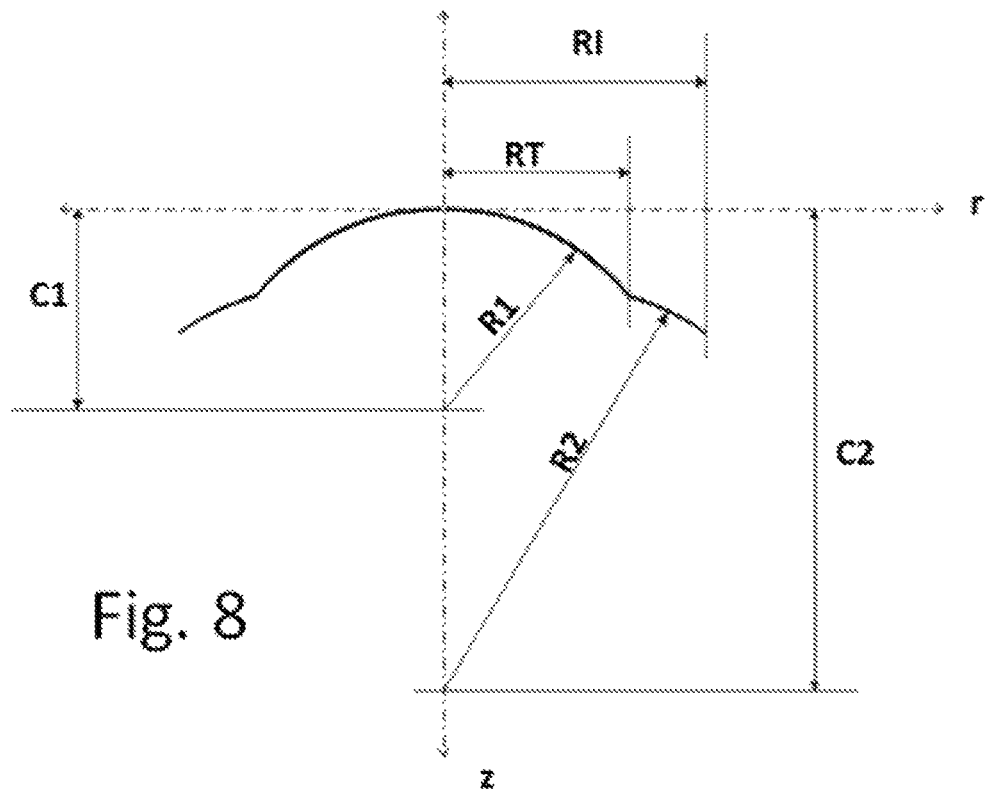
FIG. 8: Configuration 1: R1<R2, multifocal profile of the multifocal optical region with central zone for near and peripheral zone for distant vision.
Figure 9:
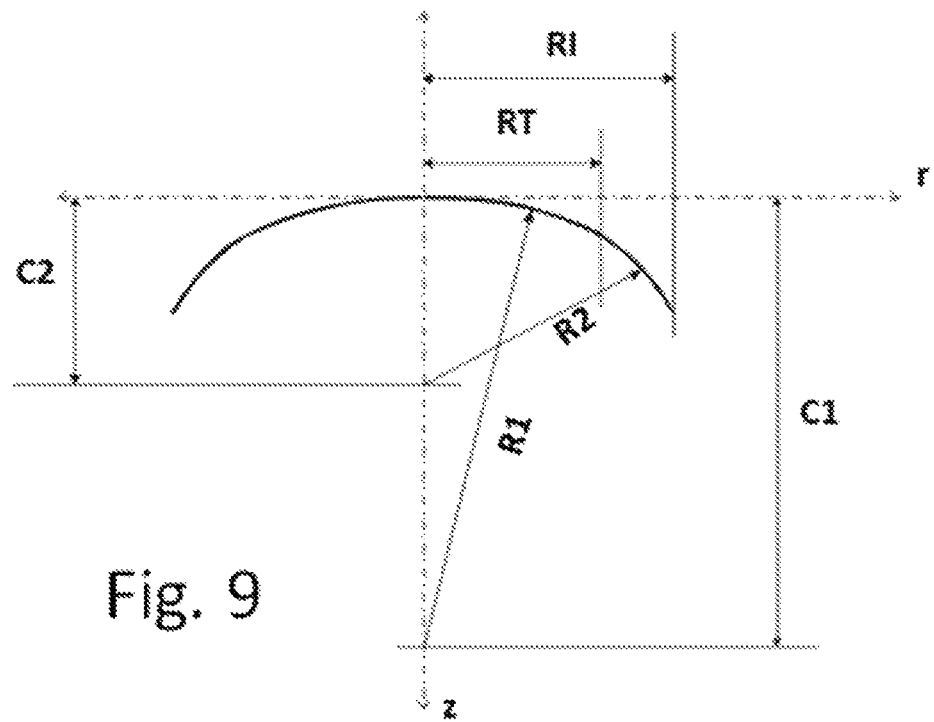
FIG. 9: Configuration 2: R1>R2, design of a lens with central zone for distant and peripheral zone for near vision.

The superior surface is determined by the next mathematical equations that describe a surface of revolution of the lens as a function of the distance to the optical axis (see FIGS. 8 and 9)

$$\text{If } r < RT \qquad z = R1 - |\sqrt[2]{R1^2 - r^2}| \qquad \text{Eq. 1}$$

$$\text{If } RM > r > RT \qquad z = C2 - |\sqrt[2]{R2^2 - r^2}| \qquad \text{Eq. 2}$$

$$\text{If } r > RM \qquad z = C3 - |\sqrt[2]{RX^2 - r^2}| \qquad \text{Eq. 3}$$

Where r and z are radial and axial coordinates respectively of a point of the surface of the lens; RT is the transition radius between zones 1 and 2; RM is the multifocal radius; R1 is the radius of central curvature and R2 is the radius of peripheral curvature. r can take values between 0 to RP which is the radius that delimits the body of the lens in the top view of FIG. 7. C3 is the center of curvature of radius RX of the profile of the surface in the zone of the mask. This radius could have values that permit focus light in the retina or any other, for instance, infinity. In this last case, an infinity radius would describe a flat surface and could allow us to reduce the size of the intraocular lens.

The curvature radius R1 has its center in the optical axis of the lens and at a distance C1=R1 which is the value established in the design of the lens. The center of the radius with curvature R2, is as weil aligned with the optical axis and its distance C2 is computed from next equation that is obtained by balancing Eq. 1 and Eq. 2 and replacing r by RT which is the radius of transition between the two curvatures (zones).

$$C2 = R1 - \sqrt[2]{R1^2 - RT^2} + \sqrt[2]{R2^2 - RT^2} \qquad \text{Eq. 4}$$

R1, R2, RX, RT and RI are parameters that define the top surface of the lens. All the previous parameters are given in mm.

FIGS. 8 and 9 show the profile of a useful optical zone that is obtained from parameters and equations before described. Outside the useful optical zone is the opaque mask (1) which has not been represented in these figures. The configuration shown in FIG. 8 is designed with the center for near vision and the periphery for distant vision (R1<R2). The opposite occurs with the configuration shown in FIG. 9 where the center is intended for far vision and the periphery for near vision (R1>R2).

As it was previously mentioned, this bifocal refractive surface can be contained in any of the two surfaces, anterior or posterior, that form the intraocular lens.

Another design that is proposed in this invention is formed by circular sectors of the lens with different curvatures inside a radius RM equal or larger than RI, the internal radius of the mask. Preferably RM=RI=2 mm. In this way, the curvature in a determine position of the multifocal optical zone of the lens depends on the angle and the magnitude of the distance to the optical axis since it is not a surface of revolution.

For $r < RM$

If $A1 < \beta < A2$ $\quad z = R1 - \left| \sqrt[2]{R1^2 - r^2} \right|$ $\quad$ Eq. 5

In any other case $\quad z = C2 - \left| \sqrt[2]{R2^2 - r^2} \right|$ $\quad$ Eq. 6

Where $\quad C2 = R1 - \left| \sqrt[2]{R1^2 - RM^2} \right| + \left| \sqrt[2]{R2^2 - RM^2} \right|$ $\quad$ Eq. 7

If $r > RM$ $\quad z = C3 - \left| \sqrt[2]{RX^2 - r^2} \right|$ $\quad$ Eq. 8

Where r and z are radial and axial coordinates respectively of a point on the surface of the lens, $\beta$ is the angle of the polar parameter r, A1 and A2 are minimum and maximum angles measured from the horizontal, on which the lens will have the curvature R1; R1 is the larger radius of curvature for distant vision and R2 is the radius of curvature for near vision. In this particular design C3 and RX are parameter that could be equal to R1 which would describe, in the zone of the mask, the same spherical surface that focus rays of light coming from infinity onto the retina. On the contrary, it could be a constant value independent of r when r>RM which would describe a flat surface. The center C2 of the radius of curvature R2 is computed from Eq. 7 which is obtained by balancing Eq. 5 and Eq. 6 and replacing r by RM which is the radius that delimits the bifocal zone.

Figure 10:
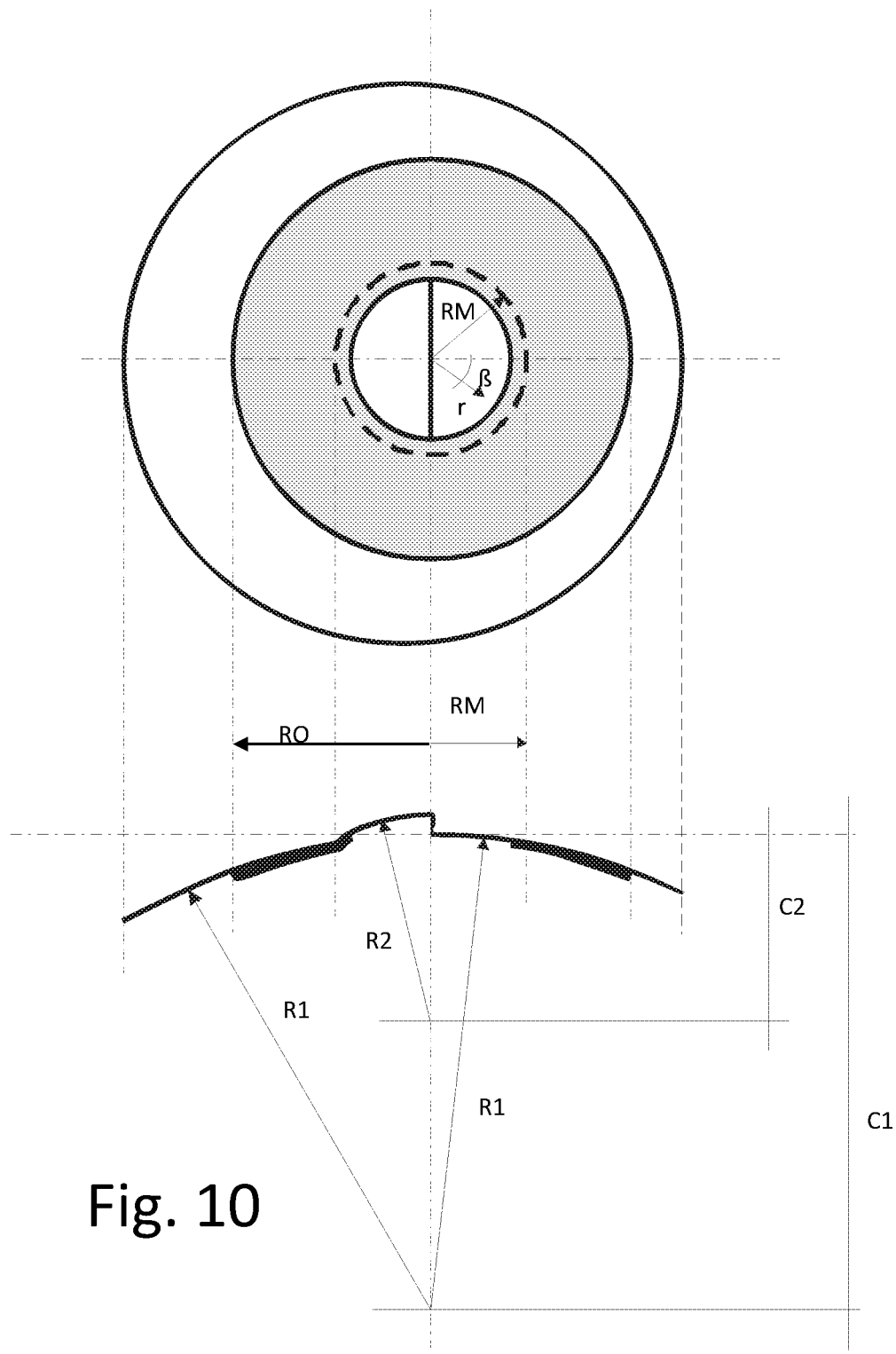
FIG. 10: Profile of refractive bifocal lens with optical sectors and mask. Superior and frontal view of the profile with light distribution 50/50. The profile has been simplified and the second surface is not shown which could be described by a spherical surface.

FIG. 10 shows the mentioned parameter. It can be seen that the radius RM is, as an example, larger than the internal radius of the mask to avoid uncontrolled optical effects although this can be equal to RI as it was exposed. In FIG. 10 it is shown a top view where the position of the polar vector r with its magnitude and angle is represented. In this figure a lens, with light distribution 50/50 for distant and near vision, has been represented, whose angles A1 and A2 are respectively −90° and 90° with respect to the horizontal axis.

This design also allows the optical axis (3) to be misaligned a maximum of 1 mm with respect to the geometrical center (4) as it can be seen in FIG. 10. A preferential design, but not limit to it, would induce a misalignment of 0.2 mm between the optical axis and the geometrical center.

As mentioned in the previous design, the multifocal profile could be in any of the two surfaces of the lens.

Haptics (6) will have certain shapes depending on if it is a lens for the capsular bag or another region of the eye.

The invention claimed is:

1. Multifocal intraocular lens with extended depth of field, comprising:
   one or more surfaces of the multifocal intraocular lens, at least one of the one or more surfaces of the multifocal intraocular lens comprising:
      a small zone with a multifocal profile with a defined optical axis, and
      in the peripheral region and coaxial to the multifocal zone, a ring-shaped opaque mask that partially or totally blocks light to produce a small aperture effect and, therefore, the multifocal profile has a radius equal or larger than the internal radius of the mask, and there is at least one transition between focal zones or one diffractive step inside the internal radius of the mask, wherein the optical axis is misaligned with respect to the geometrical center of the lens,
   wherein a superior surface of the one or more surfaces of the lens is determined by:

if $r < RT$ $\quad z = R1 - \left| \sqrt[2]{R1^2 - r^2} \right|$ $\quad$ Eq. 1 if $RM > r > RT$ $\quad z = C2 - \left| \sqrt[2]{R2^2 - r^2} \right|$ $\quad$ Eq. 2 if $r > RM$ $\quad z = C3 - \left| \sqrt[2]{RX^2 - r^2} \right|$ $\quad$ Eq. 3 wherein r is a radial coordinate of the lens, z is an axial coordinate of the lens, RT is a transition radius between zones 1 and 2, RM is a multifocal radius, R1 is a radius of central curvature, R2 is a radius of peripheral curvature, RX is a curvature of radius of the profile of the surface in the zone of the mask, C3 is the center of RX, and C2=

$$R1 - \sqrt[2]{R1^2 - RT^2} + \sqrt[2]{R2^2 - RT^2}).$$

2. Lens, according to claim 1, where the mask is located in the surface with multifocal profile.

3. Lens, according to claim 1, where the mask is located in the optical body of the lens.

4. Lens, according to claim 1, where the mask is formed by a component joint together to the optical body.

5. Lens, according claim 1, where the mask has the full thickness of the optical body.

6. Lens, according to claim 1, where the mask has a transmittance lower than 10% for a wavelength of 550 nm.

7. Lens, according to claim 1, where the internal radius of the mask is between 0.6 and 1.2 mm, the external radius is between 1.5 and 3 mm, and the multifocal profile has a radius smaller than 1.5 mm.

8. Lens, according to claim 1, where the mask has a mark for its orientation.

9. Lens according to claim 1, where the lens has a surface with a multifocal profile and an opposite spherical or aspherical surface with toricity.

10. Lens, according to claim 1, where the surface is refractive.

11. Lens, according to claim 1, whose multifocal profile has two concentric focal zones; the first one ranging from the center to the transition radius and the second with external radius equal or larger than the internal radius of the mask.

12. Lens, according to claim 11, where the optical axis is displaced 0.2 mm from the geometrical center.

13. Lens, according to claim 11, with a light distribution between focal zones ranging from 30/70 to 70/30.

14. Lens, according to claim 1, where the multifocal profile comprises two circular sectors with different curvature.

15. Lens, according to claim 14, where the optical axis is displaced 0.2 mm from the geometrical center.

16. Lens, according to claim 14, with a light distribution between circular sectors ranging between 30/70 and 70/30.

* * * * *